United States Patent [19]
Quaresima

[11] Patent Number: 5,598,230
[45] Date of Patent: Jan. 28, 1997

[54] ANTI-GLARE EYE SHIELD

[76] Inventor: James S. Quaresima, 6 Higbee Rd., Hampton Bays, N.Y. 11946

[21] Appl. No.: 552,618

[22] Filed: Nov. 3, 1995

[51] Int. Cl.$^6$ .............................. G02C 7/10; G02C 5/02; G02C 1/00; A61F 9/00
[52] U.S. Cl. ...................... 351/44; 351/124; 351/158; 2/12
[58] Field of Search ................... 351/41, 44, 140, 351/142, 147, 149, 158, 124; 2/12, 446

[56] References Cited

U.S. PATENT DOCUMENTS 4,057,852  11/1977  Contant ......................................... 2/12
4,106,119  8/1978  Taupin ........................................... 2/12

Primary Examiner—Huy Mai
Attorney, Agent, or Firm—Roylance, Abrams, Berdo & Goodman, L.L.P.

[57] ABSTRACT

An anti-glare eye shield particularly suitable for use by computer operators includes a hood portion to shield the user's eyes from overhead lighting as well as peripheral lighting, a headband, and a nose bridge support. The headband includes a coupling device for adjusting the size of the headband to accommodate different users. The bottom face of the hood portion includes a plurality of recesses for selectively receiving a nose bridge support. The nose bridge support is removably attached to the hood by inserting the nose bridge support into the appropriate recess to accommodate the facial characteristics of the user. The eye shield is particularly suitable for limiting the field of view of the user to enable to user to focus on the computer screen and reduce the incidence of eyestrain and fatigue. The shield is dimensioned to be fit over the user's glasses without discomfort.

17 Claims, 2 Drawing Sheets

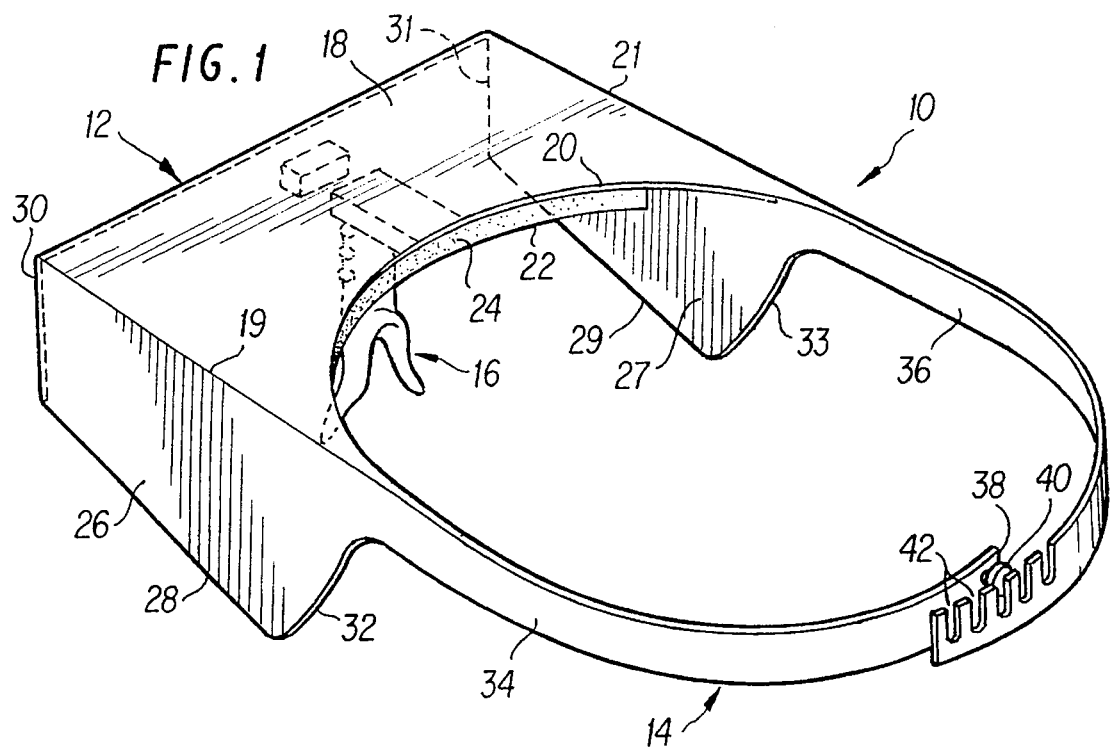
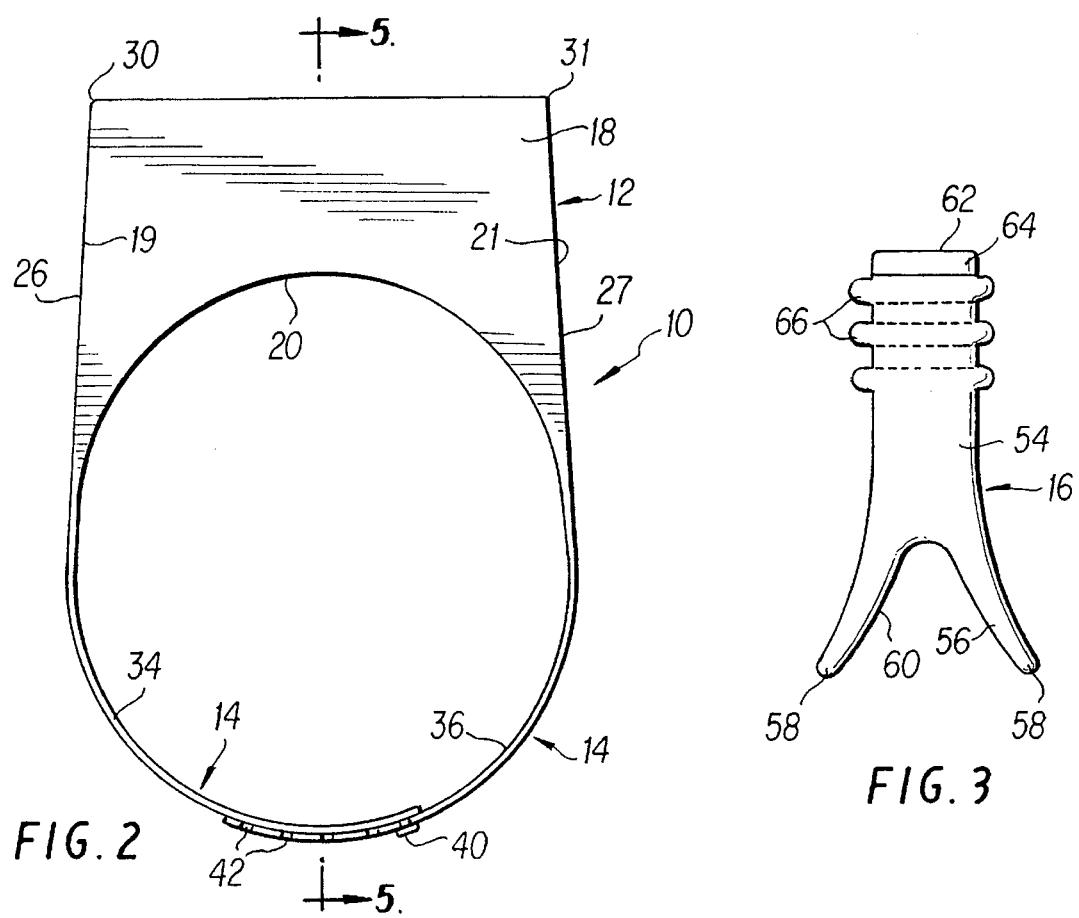

ANTI-GLARE EYE SHIELD

FIELD OF THE INVENTION

The present invention is directed to an ergonomically designed anti-glare eye shield primarily for use by computer operators. More particularly, the invention is directed to an anti-glare eye shield having an adjustable nose support to provide maximum comfort to the user.

BACKGROUND OF THE INVENTION

With the advent of computers in the office and at home has come many health problems which previously were either unknown or occurred only in few isolated cases. Daily use of computers has resulted in a variety of work-related injuries to the neck, head, arm and hand which are typically referred to as repetitive stress injuries. These injuries usually occur by performing repetitive movements or by being required to remain in a specific position for long periods of time.

Eye strain and fatigue are common problems associated with prolonged use of computers. The constant glare from the computer screens often result in eye strain, which can lead to severe headaches and other discomforts. Reflections on the computer screen from overhead lights also contribute to eye strain and fatigue. In addition, background and overhead lighting can produce glare in the computer operator's eyes which makes it difficult for the operator to focus on the computer monitor.

Numerous methods have been proposed in the past to reduce eye strain when using a computer for prolonged periods of time. These methods include such means as reducing the level of background and overhead lighting, consciously blinking frequently to keep the eyes moist and clean, maintaining regular breathing rates, and taking regular breaks. In the workplace, however, these methods are often impossible to achieve and are impractical to implement.

Numerous anti-glare eye shields and eye shades have been proposed for various purposes. For example, various eye shields have been proposed for drivers and pilots to reduce the glare from the sun or lights. Other eye shields have been proposed which serve as blinders to avoid distraction during various activities and for training exercises. Examples of these types of eye shields are disclosed in U.S. Pat. Nos. 2,933,734; 3,330,051; 3,308,498; 3,225,459 and 5,261,124. These devices do not provide adequate protection from glare and reflection from incidental light, as well as the glare from the computer terminal. Furthermore, these devices are typically bulky and uncomfortable to wear.

Numerous ergonomic products are currently available to reduce or minimize the discomfort associated with prolonged computer use. These devices are primarily directed to preventing carpal tunnel syndrome and muscle fatigue. However, these devices do not provide prevention of eye strain. Accordingly, there is a continuing need in the industry for a device for reducing eye strain caused by prolonged computer use.

SUMMARY OF THE INVENTION

A primary object of the invention is to provide an ergonomic eye shield for blocking the glare usually encountered by a computer operator.

A further object of the invention is to provide a device for shielding distractions from the view of the operator.

Another object of the invention is to provide an eye shield to enable a computer operator to tunnel their view and focus their attention on the computer monitor, thereby reducing focus stress.

A further object of the invention is to provide an eye shield for reducing eye fatigue and eye strain caused by prolonged use of a computer.

The objects of the invention are basically attained by providing an eye shield comprising a top portion having a first edge conforming to a wearer's forehead, a second edge opposite the first edge and a pair of side edges extending between the first and second edges; a side member coupled to each of the side edges and extending substantially perpendicular to the top portion; a strap coupled to each of the side members defining a head encircling band, each strap having coupling means for adjustably coupling the straps together; a nose bridge support for supporting the shield; and a plurality of spaced apart coupling means on a bottom surface of the top portion for removably coupling with the nose bridge, each of the coupling means being positioned along an axis and spaced from the first edge for selectively spacing the nose bridge from the first edge.

The objects of the invention are further attained by an anti-glare eye shield comprising a substantially planar top portion having a first edge conforming to a wearer's forehead, a second edge opposite the first edge, and a pair of parallel side edges; first and second side portions extending from the side edges substantially perpendicular to the top portion, each of the side portions having a first curved end, wherein the curved end of each side portion forms a head encircling band; a raised collar portion extending from a bottom face of the top portion and having a plurality of recesses therein positioned in a row extending away from the first edge of the top portion; and a nose bridge support having a substantially Y-shaped lower end for engaging a wearer's nose and an upper end for frictionally engaging the recesses.

Other objects, advantages and salient features of the invention will become apparent from the following detailed description which, taken in conjunction with the annexed drawings, disclose preferred embodiments of the invention.

BRIEF DESCRIPTION OF THE DRAWINGS

Referring now to the drawings, which form a part of this original disclosure:

FIG. 1 is a top perspective view of the anti-glare eye shield in a first embodiment of the invention showing the shield, nose bridge and bottom face of the shield;

FIG. 2 is a top plan view of the eye shield of FIG. 1;

FIG. 3 is a front elevational view of the nose bridge in one embodiment of the invention;

DETAILED DESCRIPTION OF THE DRAWINGS

Figure 4:
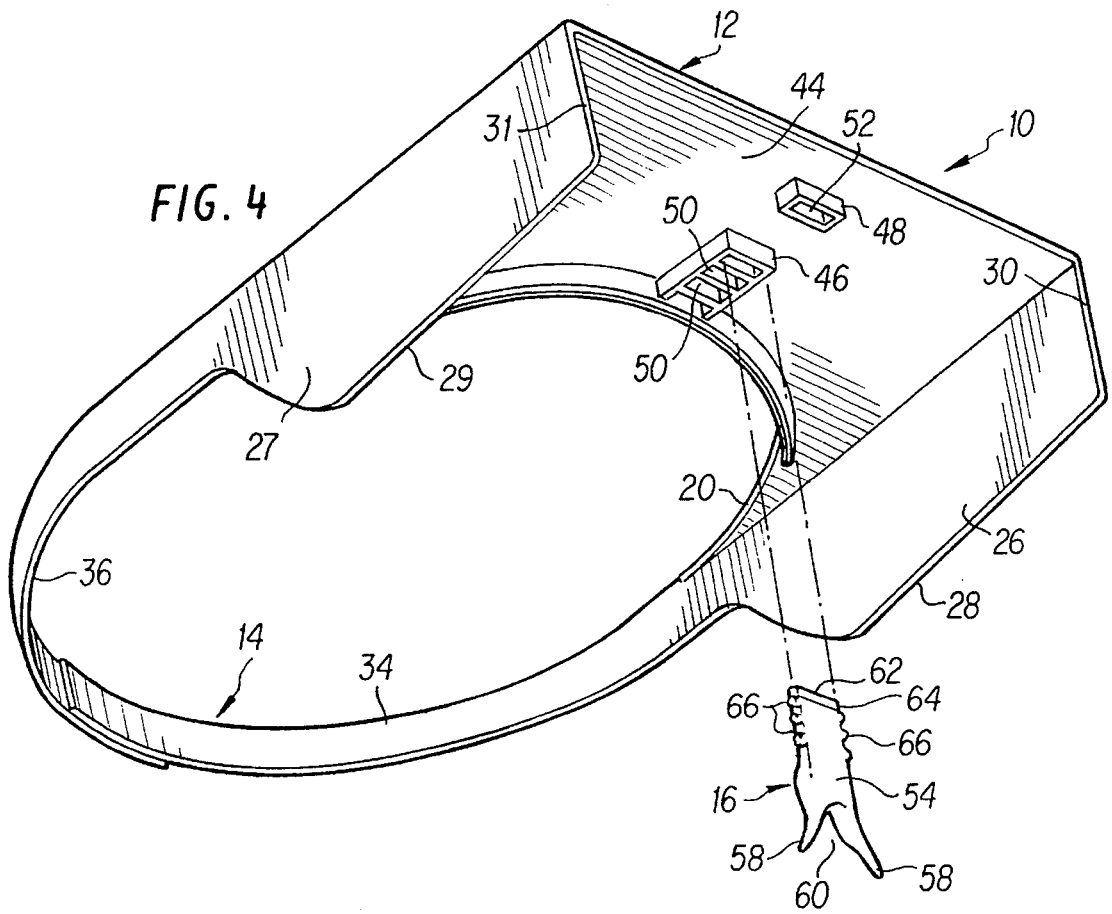
FIG. 4 is a bottom exploded perspective view of the eye shield.

The present invention is directed to an eye shield 10 particularly adapted to be worn by a computer operator to protect the operator from glare and reflection from the surrounding light. The eye shield 10 is an ergonomically designed device to shield the operator from distractions enabling the operator to focus their attention on the computer monitor. The anti-glare eye shield 10 includes a hood portion 12, a head encircling band 14, and a nose bridge support 16. The hood portion 12 is designed to shield the operator's eyes from competing light sources, thereby tunneling the operator's view to the computer screen, thereby reducing eye strain and focus stress.

The hood portion 12 of the eye shield 10 includes a substantially planar top portion 18 having a curved first inner edge surface 20 shaped to conform to and rest against the forehead of the user. A depending lip 22 extends downwardly from the first edge 20 to define a smooth surface for contacting the forehead. The depending lip 22 preferably includes a soft padding or cushion material 24 to make the device more comfortable to wear. The soft padding material 24 can be an absorbent or non-absorbent foam pad or cloth material. In the embodiment illustrated, the depending lip 22 also has a concave shape conforming to the shape of inner surface 22 and is positioned in the approximate center of the top portion 18. In alternative embodiments, the lip 22 can extend along the entire length of edge 20 to provide maximum contact with the forehead of the user.

Figure 5:
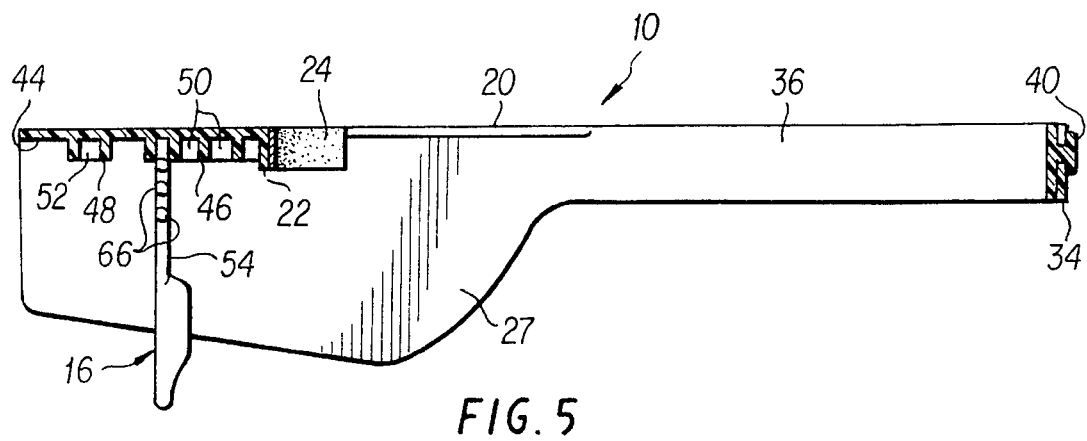
FIG. 5 is a side elevational view in cross-section taken along line 5—5 of FIG. 2.

The hood portion 12 also includes a pair of side members 26 and 27 extending substantially perpendicular to the top portion 18 along each of the opposite side edges 19 and 21, respectively, of the top portion 18. As shown in FIGS. 1, 4 and 5, each side portion 26 and 27 has a lower edge 28 and 29, respectively, tapering toward the outer edge 30 and 31, respectively. The rear edge 32 and 33 of each side portion 26 and 29, respectively, tapers to form a strap 34 and 36, respectively. Each strap 34 and 36 have a curved shape and are joined together to form the head encircling band 14. Each strap 34 and 36 include a coupling device 38 for coupling the straps together. In preferred embodiments, the coupling device 38 is a snap arrangement. In the embodiment shown in FIG. 1, the coupling device comprises a snap assembly which includes a substantially T-shaped stud 40 having an enlarged head extending from the rear side of strap 34. Strap 36 includes a plurality of spaced-apart U-shaped notches 42 for frictionally engaging the stud 40. The notches 42 are spaced apart a distance to provide adequate size adjustment to accommodate different users of the eye shield 10. In alternative embodiments, the coupling device can be any suitable fastening means including, for example, Velcro-type fasteners.

As shown in FIGS. 4 and 5, the bottom face 44 of top portion 18 includes first and second raised portions 46 and 48, respectively, forming a collar. The first raised portion 46 extends outwardly from the bottom face 44, and includes a plurality of spaced-apart recesses 50. As shown, four recesses 50 are provided having an elongated substantially rectangular shape to form a plurality of slots. The recesses 50 are equally spaced apart in a row extending axially from the inner edge 20 of the top portion 18. The second raised portion 48 is shown spaced from the first raised portion 46, and includes a single recess 52 having the shape of an elongated slot.

The nose bridge 16 has a substantially elongated planar body portion 54 with a lower end 56 having a substantially Y-shape. The Y-shaped lower end 56 is defined by a pair of legs 58 diverging outwardly to form a smooth concave inner surface 60. Nose bridge 16 also includes an upper distal end 62 having a shape complementing the shape of the recesses 50 and 52. The upper end 62 of the nose bridge 16 frictionally engages the recesses to removably attach the nose bridge 16 to the top portion 18. A plurality of stop members 66 shown as detents extend from opposite sides of the nose bridge 16 to limit the depth of insertion of the nose bridge 16 into the recesses 50, 52. The stop members 66 engage the raised collar portions 46, 48 to assist in stabilizing the nose bridge. In this fashion, the position of the nose bridge 16 can be adjusted with respect to the first edge 20 of the top portion 18 to accommodate different users of the eye shield 10. In embodiments of the invention, the upper end 62 includes a resilient friction enhancing member 64 to assist in retaining the nose bridge 16 in the recesses 50 and 52. The friction enhancing member 64 can be a resilient rubber-like material or padding. The nose bridge 16 fits securely within the recesses 50 and 52 while allowing some side-to-side swinging adjustment to allow the device 10 to fit comfortably.

In embodiments of the invention, the nose bridge support 16 includes a plurality of frangible lines 66 extending across the body portion 54. In this manner, the length of the body portion 54 can be shortened by breaking the body portion along the frangible lines 66, and thus shortening the nose bridge 16 to accommodate the particular needs of the user.

In further embodiments, a tinted shield or shade (not shown) can be attached to the bottom surface of the hood portion in front of the user's eyes. The tinted material can be, for example, a standard tinted transparent material used for manufacturing sunglasses. The amount of tinting in the shield can vary, depending on the intended use of the device. The shield is preferably attached to the hood portion in the same manner as the nose bridge support. The shield can include a leg having an end portion dimensioned to press fit into the recesses in the bottom face of the hood portion. In particular, the shield can be attached in the recess spaced closest to the front edge.

In use, the straps 34 and 36 are coupled together by the coupling device 38 so that the head encircling band 14 fits the head of the user. The nose bridge 16 is then placed in the appropriate recess 50 or 52 so that the lower end 56 of the nose bridge contacts the nose of the user to support the top portion 18 of the eye shield. If necessary, the length of the nose bridge can be adjusted to accommodate the needs of the user to properly support the eye shield.

The top portion 18 and side portions 26 are dimensioned to shield the user's eyes from glare and reflected light in the working environment. In particular, the eye shield 10 is dimensioned to be able to block overhead lighting which may interfere with the ability of the user to focus on the computer screen. The side portions 26 also block the user's view of any distracting activity occurring around the worksite to enable the user to properly focus on the computer screen. In preferred embodiments, the inner surfaces of the top portion 18 and side portions 26 and 27 have a non-reflective surface to further reduce distractions by reflected light.

The eye shield 10 of the invention is able to be comfortably worn by the user and is able to accommodate a variety of facial features. The eye shield is also able to be worn by the user without interfering with the user's eyeglasses since the shield 10 is dimensioned to fit over the user's glasses and the nose bridge 16 can be positioned to avoid interfering with the glasses. The eye shield is particularly suitable for people wearing glasses to reduce peripheral glare and to reduce the amount of reflected light on the front and rear surfaces of the lenses.

In embodiments of the invention, the eye shield is an integrally molded article made of flexible plastic but rigid enough to retain its shape. The hood 12 and head encircling band 14 are preferably formed as a single piece. Typically, the eye shield is made using standard injection molded techniques as known in the art.

The eye shield 10 is primarily directed for use by people who spend large amounts of time at computer terminals to minimize the incidence of eye strain and fatigue. The shield can have alternative uses, such as, for example, training exercises where limiting the field of view is desired.

While advantageous embodiments have been chosen to illustrate the invention, it will be understood by those skilled in the art that various changes and modifications can be made therein without departing from the scope of the invention as defined in the appended claims.

What is claimed is:

1. An anti-glare eye shield comprising a top portion having a first edge conforming to a wearer's forehead, a second edge opposite said first edge and a pair of side edges extending between said first and second edges;

a side member coupled to each of said side edges and extending downwardly substantially perpendicular to said top portion;

a strap member coupled to each of said side members, wherein said strap members define a head encircling band, each strap member having coupling means for adjustably coupling said strap members together;

a nose bridge for supporting said shield; and a plurality of nose bridge coupling means on a bottom surface of said top portion for removably coupling with said nose bridge, each said nose bridge coupling means being positioned along an axis and spaced from said first edge for selectively spacing said nose bridge from said first edge.

2. The eye shield of claim 1, wherein said top portion is a substantially flat planar body.

3. The eye shield of claim 1, wherein said nose bridge coupling means on said top portion comprises a plurality of spaced-apart recesses, for receiving said nose bridge.

4. The eye shield of claim 3, wherein said top portion includes a collar surrounding said recesses.

5. The eye shield of claim 3, comprising a projecting portion on said bottom surface of said top portion and said recesses being formed in said projecting portion.

6. The eye shield of claim 1, wherein said nose bridge includes a substantially Y-shaped nose engaging portion and an elongated body portion having a distal end for coupling with said nose bridge coupling means on said top portion.

7. The eye shield of claim 6, wherein said distal end of said nose piece includes a friction enhancing means.

8. The eye shield of claim 7, wherein said friction enhancing means is a resilient member.

9. The eye shield of claim 1, wherein said top portion, side members and strap portions are integrally formed and made of plastic.

10. The eye shield of claim 1, wherein said coupling means on said strap members comprise a snap.

11. An anti-glare eye shield comprising a substantially planar top portion having a first edge conforming to a wearer's forehead, a second edge opposite said first edge, and a pair of parallel side edges;

first and second side portions extending from said side edges substantially perpendicular to said top portion, each said side portion having a first curved end, wherein said curved end of each side portion forms a head encircling band;

a raised collar portion extending from a bottom face of said top portion and having a plurality of recesses therein positioned in a row extending away from said first edge of said top portion; and a nose bridge having a substantially Y-shaped lower end for engaging a wearer's nose and an upper end for frictionally engaging said recesses.

12. The eye shield of claim 11, wherein said bottom face of said top portion comprises a second raised collar portion spaced from said first raised collar portion.

13. The eye shield of claim 11, wherein said recesses are a plurality of elongated slots.

14. The eye shield of claim 13, wherein said upper end of said nose bridge has a substantially rectangular cross-section complementing the dimension of said elongated slots.

15. The eye shield of claim 12, wherein said upper end of said nose bridge comprises resilient friction enhancing members.

16. The eye shield of claim 11, wherein the curved ends of said side portions include a coupling means.

17. The eye shield of claim 16, wherein said coupling means on said side portions comprises a snap.

* * * * *